United States Patent
Casals Terré et al.

(10) Patent No.: US 10,041,931 B2
(45) Date of Patent: Aug. 7, 2018

(54) MICROFLUIDIC DEVICE FOR SEPARATING LIQUID FROM THE SAME LIQUID CONTAINING DEFORMABLE PARTICLES WITHOUT EXTERNAL SOURCES OF ENERGY

(71) Applicant: UNIVERSITAT POLITÈCNICA DE CATALUNYA, Barcelona (ES)

(72) Inventors: Jasmina Casals Terré, Barcelona (ES); Hojjat Madadi, Barcelona (ES)

(73) Assignee: UNIVERSITAT POLITÈCNICA DE CATALUNYA, Barcelona (ES)

( * ) Notice: Subject to any disclaimer, the term of this patent is extended or adjusted under 35 U.S.C. 154(b) by 0 days.

(21) Appl. No.: 15/154,937

(22) Filed: May 13, 2016

(65) Prior Publication Data
US 2016/0258928 A1 Sep. 8, 2016

Related U.S. Application Data

(63) Continuation of application No. PCT/ES2014/070833, filed on Nov. 11, 2014.

(51) Int. Cl.
*G01N 27/447* (2006.01)
*G01N 33/49* (2006.01)
*B03C 5/02* (2006.01)

(52) U.S. Cl.
CPC ........... *G01N 33/491* (2013.01); *B03C 5/022* (2013.01); *G01N 27/44791* (2013.01)

(58) Field of Classification Search
CPC . G01N 33/491; G01N 27/44791; B03C 5/022
See application file for complete search history.

(56) References Cited

U.S. PATENT DOCUMENTS

2004/0232074 A1  11/2004  Peters et al.
2011/0011781 A1  1/2011  Blankenstein et al.

FOREIGN PATENT DOCUMENTS

WO    WO 2005/095954       10/2005
WO    WO 2007/071989 A1    6/2007
(Continued)

OTHER PUBLICATIONS

Kim, et al. "Plasma extraction in a capillary-driven microfluidic device using surfactant-added poly(dimethylsiloxane)," Sensor and Actuators, B, vol. 145, 2010, p. 861-868.*
(Continued)

*Primary Examiner* — J. Christopher Ball
(74) *Attorney, Agent, or Firm* — Robert J. Hess; Hess Patent Law Firm (57) ABSTRACT

A microfluidic device for separating liquid from the same liquid containing deformable particles without external sources of energy. The device includes: at least one transport channel (1) using various fluid-hydrodynamic principles in order to increase the amount of separated/obtained fluid; and at least one separating area (2) which diverts part of the fluid circulating through the transport channel towards at least one collection channel (3) or reaction chamber. The separating area (2) can include at least one array of pillars, the configuration of which maximizes the amount of fluid extracted at once. The depth and width of the collection channel (3) are adaptable according to the requirements of the test to be implemented. A filter is provided for separating plasma from a drop of blood in a highly efficient manner, which can be used in point-of-care testing systems.

10 Claims, 8 Drawing Sheets

(56) References Cited

FOREIGN PATENT DOCUMENTS

| WO | WO 2009/140326 A2 | 11/2009 |
| WO | WO 2012/125723 A2 | 9/2012 |
| WO | WO 2015/071515 A1 | 5/2015 |

OTHER PUBLICATIONS

Kersaudy-Kerhoas, et al. "Micro-scale blood plasma separation: from acoustophoresis to egg-beaters," Lab on a Chip, vol. 13, 2013, p. 3323-3346*

* cited by examiner

MICROFLUIDIC DEVICE FOR SEPARATING LIQUID FROM THE SAME LIQUID CONTAINING DEFORMABLE PARTICLES WITHOUT EXTERNAL SOURCES OF ENERGY

FIELD OF THE INVENTION

The present invention relates to a microfluidic device separating particles from the liquid in which the particles are contained, maximizing the amount of liquid extracted from an initial mixture. More specifically, the present invention can separate plasma from a drop of blood to be part of a portable blood analysis device.

STATE OF THE ART

Nowadays, considerable progress has been made in the field of microfluidics, especially for chemical, biological and biomedical applications. In fact, point-of-care testing products could not be developed were it not for this technology. Most attempts made by researchers in these years have been focused on developing a microfluidic chip for separating plasma from blood, but although many attempts have been made, there are still many challenges to be met, such as improving efficiency (the amount of plasma taken) without hemolysis (the rupture of red blood cells).

The use of microfluidics not only increases convenience due to the small size, but also expedites test results.

In traditional tests, blood samples sit for a great length of time before all the processes are completed. This increases the possibilities of errors and renders the blood to be in sub-optimal conditions.

The new diagnostic tests can be more accurate, since the use of microfluidics allows using a drop of blood that has just been taken, so it is fresher, and since it is not manipulated errors are minimized and results are obtained faster.

Blood is used in many analyses to detect a broad range of illnesses. Before that, however, the elements of blood are separated: plasma (serum and fibrinogen), red blood cells, white blood cells and platelets. Normal blood is made up of 45% red blood cells, 1% white blood cells, 0.5% platelets and the rest is plasma. Red blood cells are disk-shaped deformable cells with a diameter of 8 microns and a height of 2 microns. White blood cells have a diameter between 8 and 12 microns and prevent infections. Platelets are the other main blood component and they aggregate to form clots. All these particles are suspended in plasma, which consists of 90% plasma and is yellowish in color. Besides water, plasma contains small particles (between 1 and 3 microns in diameter) that are basically serum, albumin, clotting factors, hormones, carbon dioxide, proteins, electrolytes and immunoglobulin.

Separating plasma from blood today is done by means of laboratory centrifugation and relatively large volumes (milliliters) of blood are required, or it is done by means of sedimentation but this process is very slow.

In order to minimize errors, reduce the time between extraction and obtaining test results, "lab-on-a-chip" type devices are of interest for separating plasma from blood and subsequently performing the test. Researchers have developed plasma separation systems using different techniques in microfluidics, such as cross-flow filtration, deterministic lateral displacement, dielectrophoretic techniques, constricted flow, or biomimetic separation, but most of these techniques require a pressure source or pump which users of a point-of-care test may not have available to them.

There is another group of scientists who have focused on developing microfluidic filters without external sources, but the volume of plasma extracted before the inlet into the separating channel clogs is minimal and not enough to perform blood analyses.

Accordingly, providing a device that could separate the maximum amount of liquid from a liquid containing deformable particles would be desirable.

Ralf-Peter Peters et al. U.S. Patent Application Publication No. US 2004/0232074, disclose a microstructured separating device that separates plasma from blood. The microstructure includes a straight transport channel through which the blood circulates, a separating channel at a branch point of the transport channel which is adjoined thereto perpendicularly and having a different depth. The plasma circulates in this branch point. This separating channel has a microstructure which retains the larger particles and slows down the smaller particles (chromatographic effect, i.e., the liquid transporting the particles tends to move faster than the particles do.). If the separating channel has a depth exceeding the particles to be filtered or if the particles are deformable and can enter same, the quality of the filtered liquid is not 100% free of particles. However, if the recess of the filtration area has a depth that is less than the particles to be filtered, there is no mechanism to prevent the inlet from clogging, such that the larger particles will close the inlet, limiting the amount of fluid that can be extracted. The high concentration of particles in blood (45% red blood cells) causes the separation due to the chromatographic effect to lead to a very limited plasma extraction, and most likely insufficient to implement blood tests. Furthermore, the design proposed in this patent is based on making channels having different depths in a single part and covering the channel with a cover, resulting in a complex manufacturing process.

Jee-Hoon Seo et al., International Patent No. WO 2005/095954, disclose another filter design that does not use membranes or other devices to separate plasma from blood. The filter consists of a substrate including a channel. Said channel has an inlet and at least two outlets separated from one another by a certain angle, and a set of rectangular structures (pillars) placed in the main channel at a certain angle with respect to one another. The rectangular structures in the channel allow separating plasma from blood according to the arrangement thereof. Although this invention provides a design for separating plasma from blood, the separation efficiency is not altogether good (a fair amount of particles are found in the outlet channel); due to the fact that the distance between pillars is about 10 microns and red blood cells can deform, the latter can get through the pillars near the outlet.

The goal of the present invention is to create a microfluidic chip that can be part of point-of-care testing devices that, with a single drop of blood, can separate a sufficient amount of plasma without the need of external forces to perform high-quality analyses (>90% without cells) and in a reasonable time (a matter of minutes).

Another key aspect compared to previous patents is that the amount of volume extracted from the initial volume is maximized. This is achieved due to the fact that the present invention considers the rheological behavior of red blood cells in the transport channel and delays clogging of the inlet at least until the collection channel/chamber is filled. This delay is achieved acting on two points: first, the collection channel is filled faster than in earlier designs since the separating area is designed based on a high-efficiency capillary pump, in addition to having suitable hydrophilic behavior. Secondly, the concentration of red blood cells at the inlet to the separating area is minimized, which instead of being placed on one side of the transport channel as in patent No. US 2004/0232074, is placed symmetrically on both side of the transport channel. This compensates for the capillary forces acting on the red blood cells circulating in the transport channel, such that their path is not affected and the problem of clogging of the inlet into the separating area is reduced. Thirdly, if needed electrodes could be placed at the inlet and outlet of the channel to apply electrophoretic forces on the red blood cells, forcing them to move away from the inlet into the separating area.

Another goal of the present invention is to present a device that can be mass-produced using different manufacturing process. For this purpose the device has been split into two parts: the transport and separating channels are located in one part and the separating area in another. This feature, which is not disclosed in the other patents, could largely aid the production thereof.

BRIEF DESCRIPTION OF THE INVENTION

This invention consists of a microfluidic device 100 for separating deformable particles from a liquid containing them without external forces by means of filtration outside the plane of the channel. The microfluidic device is made up of two parts: a first part (101) comprising at least one transport channel (1) using various hydrodynamics principles to maximize the volume of liquid separated by the device (100), and a second part (102) containing at least one separating area (2) filtering the particles and acting as a capillary pump in order to drive the fluid to the collection channel (3), which can be one or more in number and have a depth that is adaptable depending on the sensitivity needs of the test to be implemented.

The separating area can include an array of pillars (which can have different shapes and can also be arranged depending on the amount of fluid to be extracted). If the amount of liquid extracted is not enough to perform the test, the device allows placing two electrodes (4 and 5) at the inlet and outlet in order to drive the red blood cells away from the inlet into the separating area and thereby allow an extraction of more fluid.

The invention consists of a main channel (for transporting the liquid including the particles), which includes at least one constriction (1b), at which point or after which point the main channel is diverted and is connected to a filtration channel/area (2) located outside the plane of the transport channel. The particle-free fluid circulates through the channel (2). The constriction (1b) increases local speed of the particle and delays the inlet of the separating channel/area (2) from clogging, whereby increasing the amount of fluid that can be separated.

Figure 5:
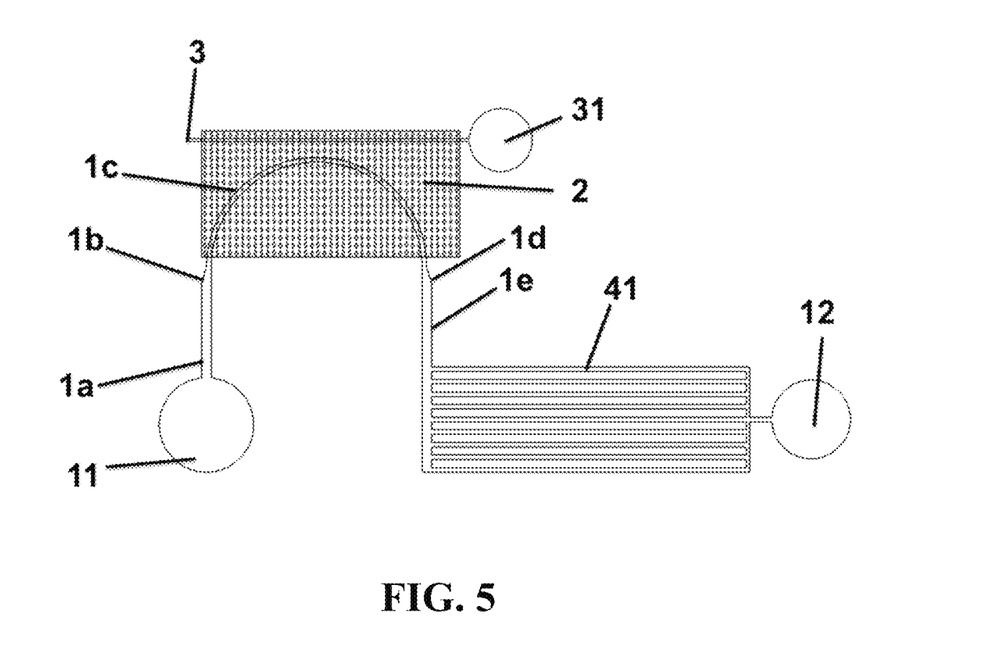
FIG. 5 shows a plan view of the invention to which a capillary pump (having parallel channels) has been added to promote flow in the main channel.
Figure 6:
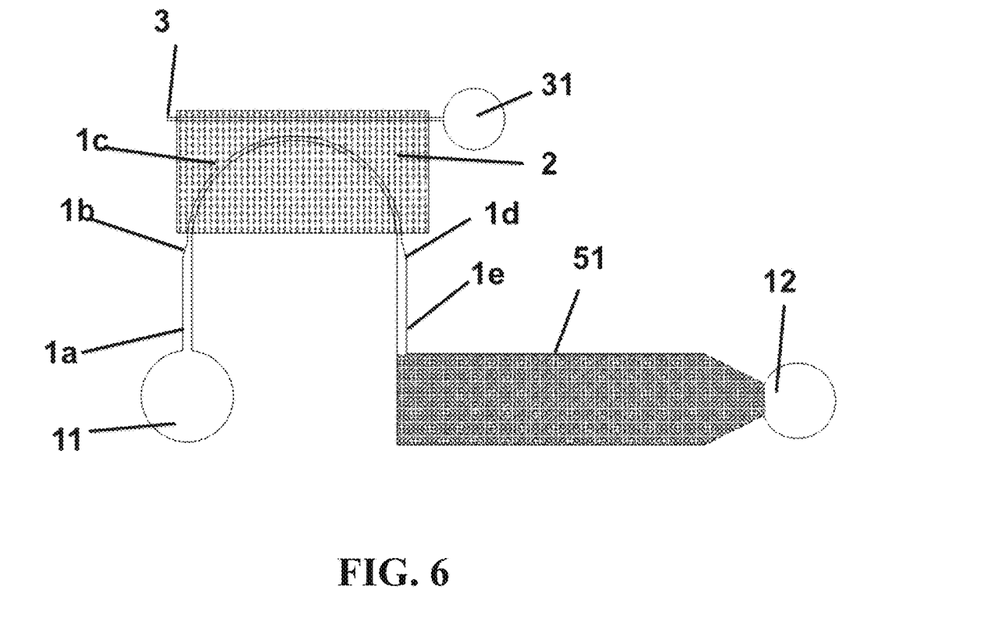
FIG. 6 shows a plan view of the invention to which a capillary pump (array of pillars) has been added to promote flow in the main channel.

In another design of the invention, the main channel (1) is extended after the separation by a capillary micropump which consists of a set of parallel channels (41) in FIG. 5 or an array of pillars (51) in FIG. 6. In these designs, the capillary forces promote greater flow in the channel such that the possibility of the inlet into the separating area being clogged is reduced.

The design of the invention has several advantages over earlier designs for separating particles from a liquid containing them, maximizing the amount of liquid that is extracted. On one hand, the design does not require external actuation, i.e., the capillary forces are enough to transport the liquid through the channels. The capillary force is achieved through the hydrophilicity of the material by either modifying hydrophobic materials such as PDMS (with hydrophilic coatings or $O_2$ plasma treatments) or by directly using hydrophilic materials. If a hydrophobic material such as polydimethylsiloxane (PDMS) is used, nonionic surfactants can be applied to compensate for its hydrophobicity.

This invention minimizes the concentration of red blood cells at the inlet into the separating area, so for this reason the depth of the separating area (H2, FIG. 1b) is less than the depth of the main channel (H1, FIG. 1b), and clearly less than the diameter of the particles to be filtered. Therefore, the quality of the filtered liquid is better than in earlier designs, many of which had depths that were greater than the size of the particle to be filtered. Furthermore, when considering obtaining plasma from blood, the deformability of red blood cells makes it necessary to restrict the depth H2 between 0.5 and 2 microns.

Figure 7:
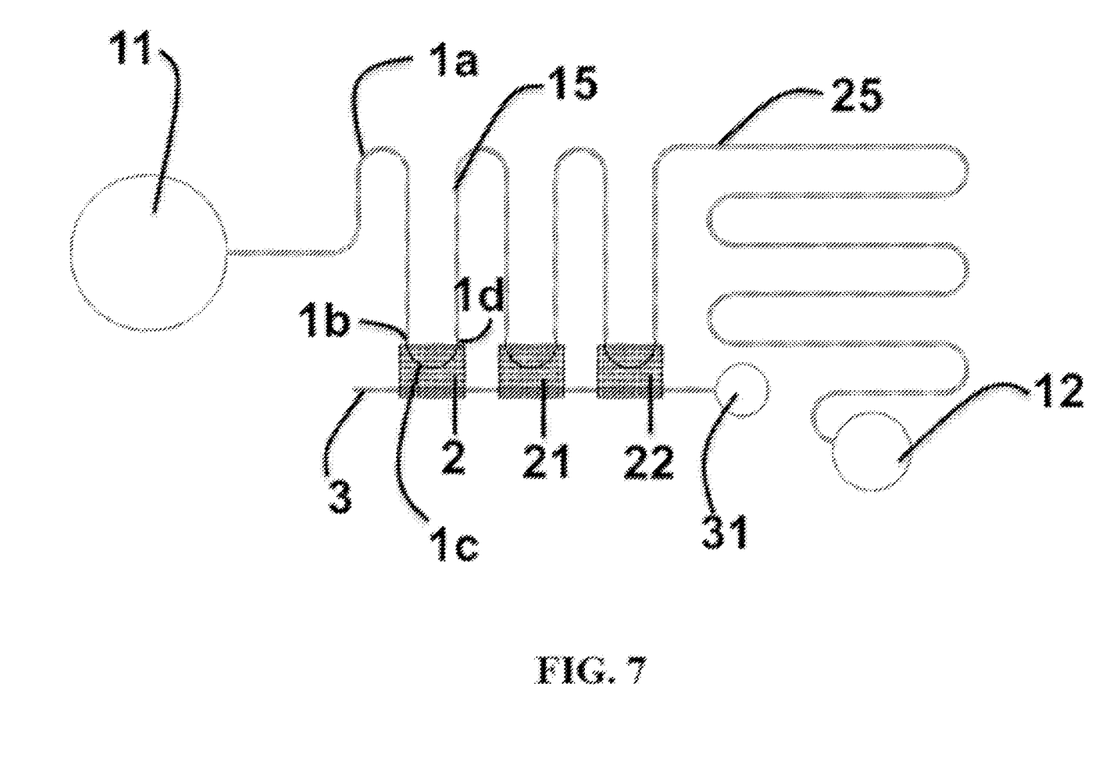
FIG. 7 shows a plan view of the invention with three separating areas.
Figure 8:
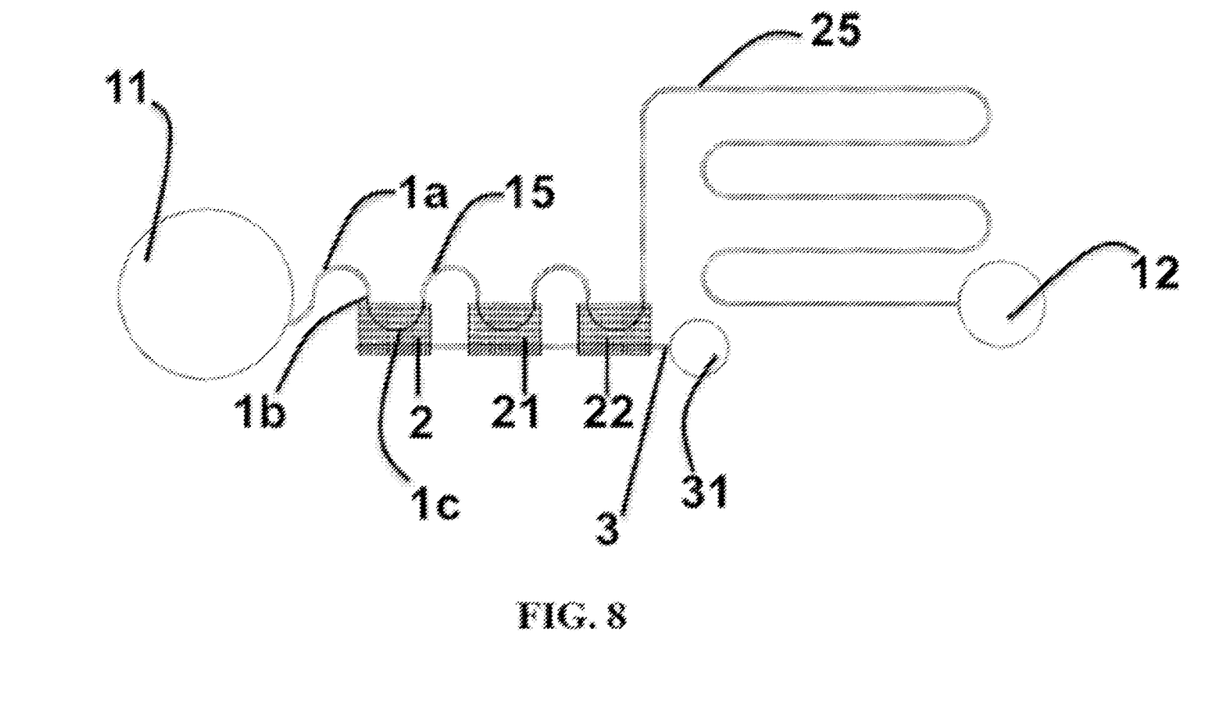
FIG. 8 shows a plan view of the invention with three separating areas with reduced length of the main channel after each separating area.
Figure 9:
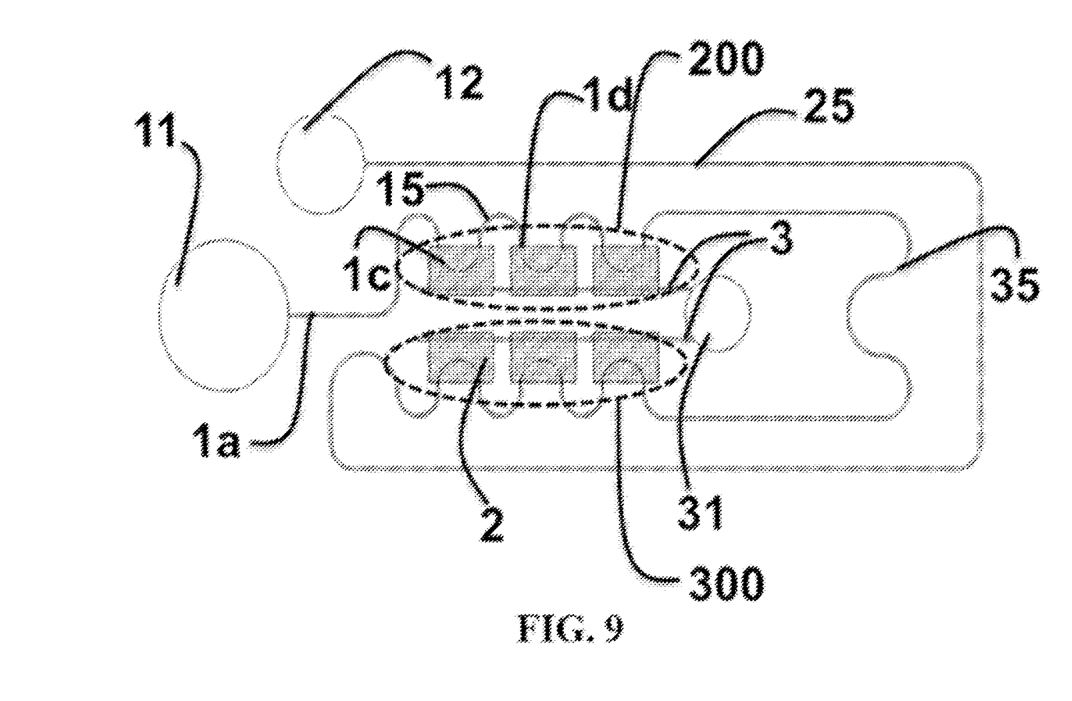
FIG. 9 shows a plan view of the invention with six separating areas to increase the amount of liquid that is extracted.

The design of the device can also have several separating areas located one after the other, e.g. see FIGS. 7, 8 and 9, where these areas are 21 and 22.

In order to collect the filtered plasma, the device has a collection channel (3) which collects the output of the different separating areas. In a point-of-care testing device, the reagents for performing the test could be located in this channel (3), or otherwise the filtered liquid could be collected with a syringe.

BRIEF DESCRIPTION OF THE DRAWINGS

The invention is described based on the following drawings.

DETAILED DESCRIPTION

Figure 1A:
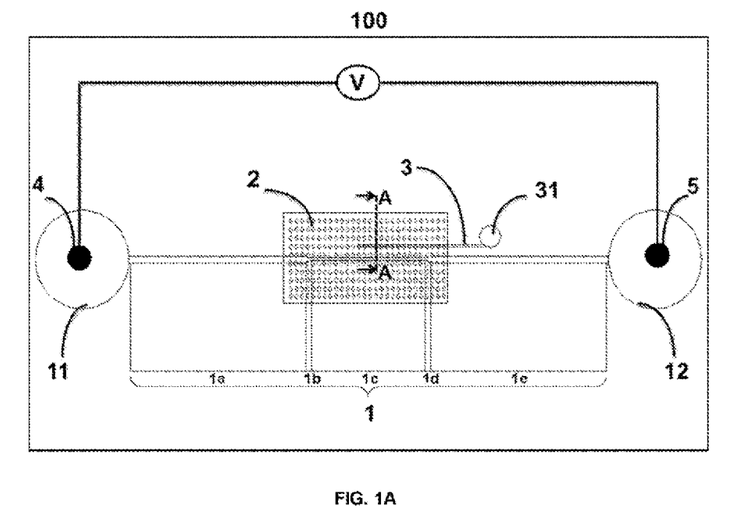
FIG. 1A shows an overall view of the microfluidic design claimed in the invention.
Figure 2:
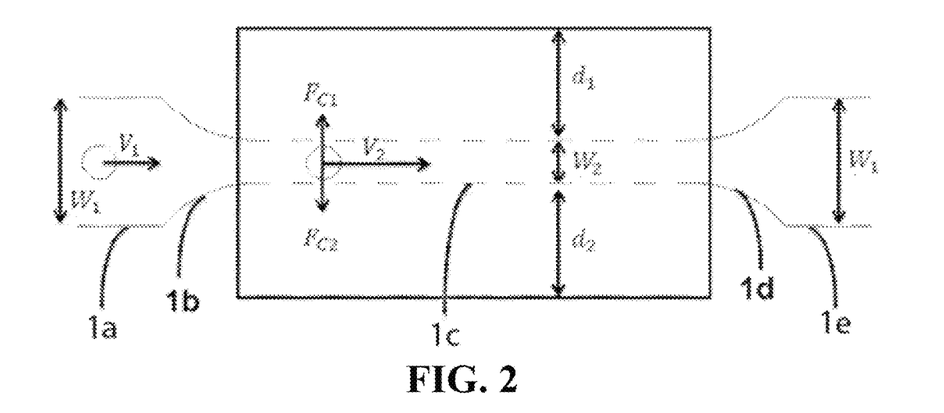
FIG. 2 is a schematic illustration of the increase in speed the particles are subjected to in the constriction in the main channel to avoid particles from building up in the filtration area. The progressive constriction for preventing damage to biological particles and the capillary forces applied to the particles as they go through the separating area are furthermore shown.

FIG. 1A illustrates a first version of the microfluidic device which has a straight transport channel (1) with an inlet port (11) and an outlet port (12), a primary main flow channel (1a) having a width w1 is linked through a constriction (1b) to an intermediate channel (1c) having a smaller width w2 which later returns to being a channel (1e) having the normal width w1 through another transition or constriction (1d). These two transitions (1b) and (1d) can have inner walls straight or curved, as shown in FIG. 2, to reduce the risk of damaging biological particles (cells). These two transitions provide a smooth reduction of the flow from 1a to 1c or 1c to 1e. Specifically in blood cells, hemolysis (the rupture of red blood cells) increases due to the induced stress in the constriction.

For most of its length, the transport channel (1c) having a smaller width is covered by a separating area (2) acting a filter which is constituted by a recess machined in first part (101). In the case of blood, the blood plasma which is to be separated flows through this separating area (2) which is also connected to a collection channel (3) where the blood analysis will be implemented. The filtered liquid is collected from the separating area by a collection channel (3) that is connected to the environment through an extraction port (31) or a test area. A syringe pump can be connected to the extraction port (31) in order to remove the separated blood plasma from the collection channel (3) if needed. If it were necessary to increase the extraction time, electrodes 4 and 5 can be placed to apply alternating electrical forces on the particles to prevent obstruction of the inlet into the separating area.

Figure 1B:
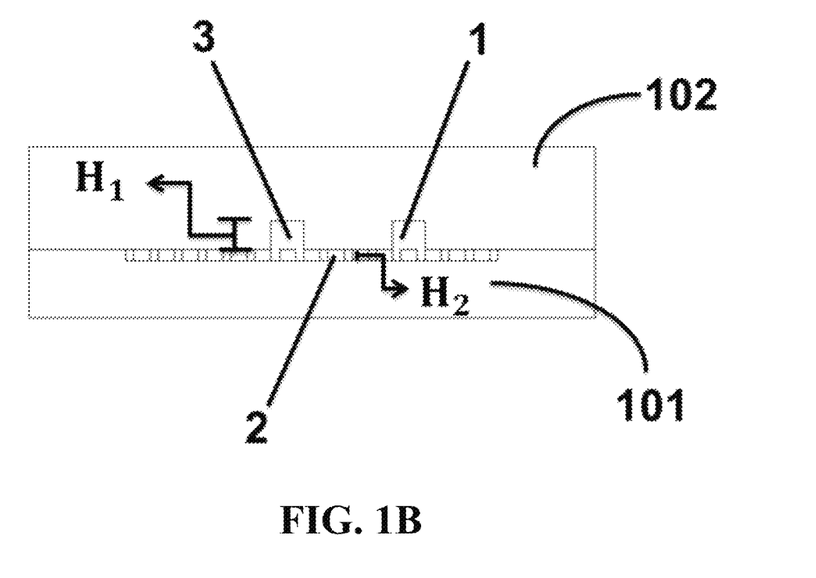
FIG. 1B shows a cross section along the section plan A-A- of the design through the filtration area.
Figure 1C:
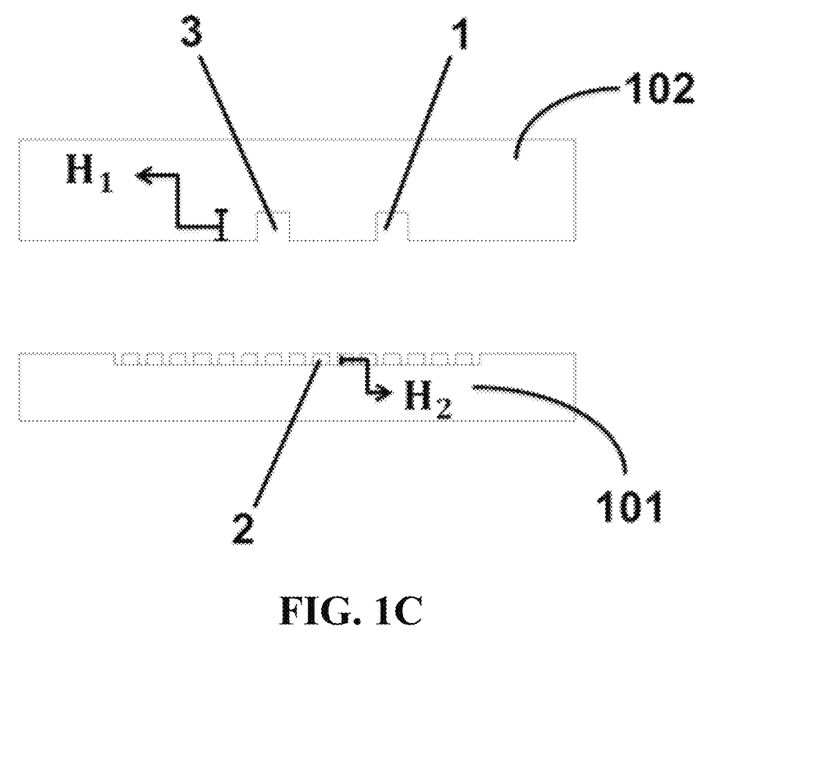
FIG. 1C is equivalent to FIG. 1B but with the first and second parts of the microfluidic device separated.

FIGS. 1B and 1C show a cross section of the separating device in which the transport channel (1) and collection channel (3) are machined in a second part (102). The separating area can include an arrangement of micropillars (2) and is machined in the first part (101). The depth H2 is set according to the size of particles to be filtered, whereas depth H1 of the channels 1 and 3 in the second part (102) is set according to the thickness of the liquid required by the test to be performed.

The capillary forces in the separating area 2 are greater than in the transport channel 1c having a smaller width such that the rate of flow of the sample in the main transport channel 1 is slowed down with respect to the rate of flow of the liquid that is extracted/filtered in the separating area 2, therefore the surface for entering the separating area 2 may be locked due to particle build-up. To solve the blockage problem, the main transport channel has a constriction (1b and 1d) to increase the rate of flow of the particles when they go below the separating area. FIG. 2 illustrates the hydrodynamics principles used to prevent blockage at the inlet into the separating area. Particularly when separating plasma from blood, red blood cells tend to migrate into the vessels and leave the region adjacent to the vessel wall free of particles (known as plasma skimming.) Furthermore, when a vessel branches into two, blood cells tend to move in the branch having the higher rate of flow and leave the branch having the lower rate of flow, which effect is known as branching. In addition to these two phenomena, the reduced section of the transport channel used in the present invention and the symmetrical distribution of the separating area mean that it takes longer for particles to build up at the entry into the channel.

FIG. 2 illustrates the fact that the extraction of plasma from blood is increased due to the use of a symmetrical filtration channel design ((d1=d2, see FIG. 2), which causes counteracting the cross capillary forces in the opposite direction, resulting in an unnoticeable force on the red blood cells circulating through the transport channel, and accordingly reduces blockage and increases extraction of plasma.

Figure 3:
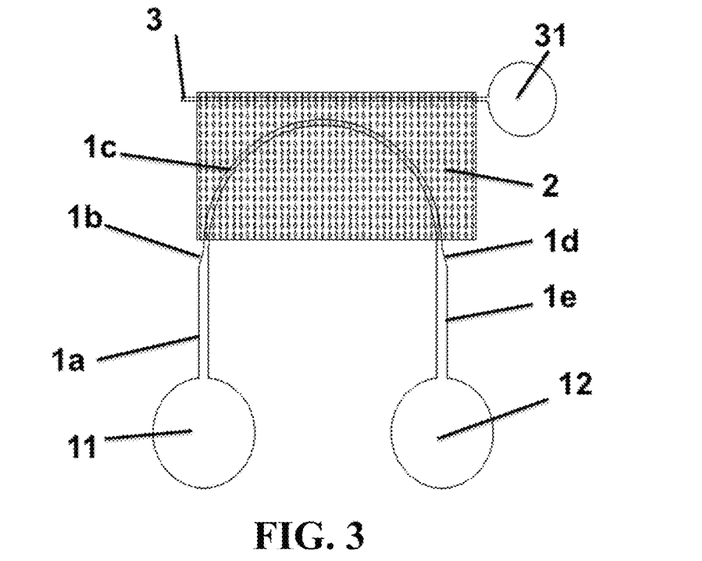
FIG. 3 shows a plan view of another version of the invention in which the main channel is curved.

FIG. 3 illustrates another version of the microfluidic device in which the direction of the flow in the main channel 1a is parallel to the flow in the separating area 2 to increase the microdevice throughput. This has been achieved by construction of the transport channel with a curved shape. The blood plasma (extracted liquid) flows through the separating area faster than in the first version of the microdevice because the direction of flow is the same as in the separating area, but the filling time of the collection channel will increase because of the red blood cells blocking the inlet into the separating area due because the centrifugal force applied on these cells make them build up at the inlet into the separating area. Electrodes 4 and 5 can be used for applying alternating electrophoretic forces on the red blood cells to prevent blockage.

Figure 4:
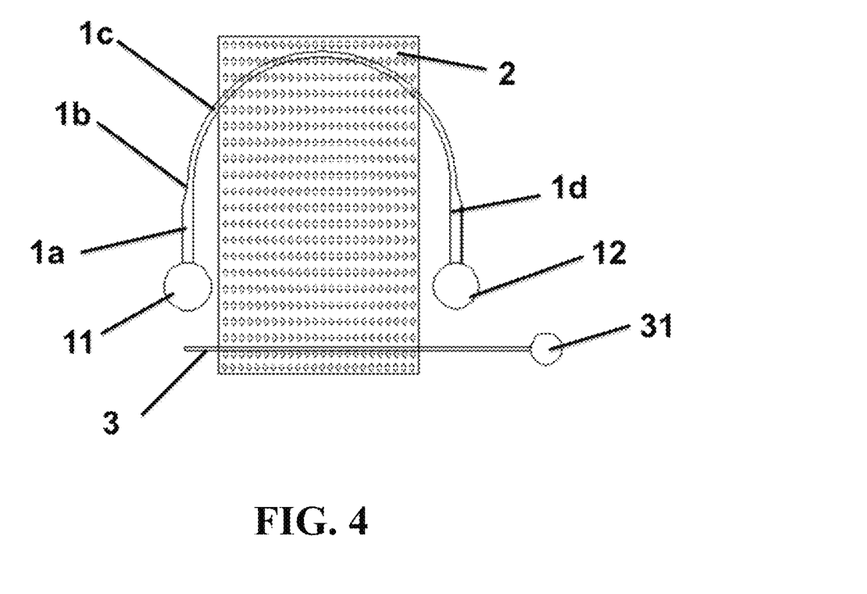
FIG. 4 shows a plan view of another version of the invention in which the main channel is curved and the collection channel is located on the side opposite the plasma flow direction.

FIG. 4 illustrates a modified version of the microdevice mentioned in FIG. 3. In this case, the transport channel is also curved, but the collection channel is placed below the inlet and the outlet. Then the centrifugal force acting on the red blood cells/particles moves them away from the separating area. The extracted plasma or liquid flows through the separating area more slowly than in the version of the microdevice in FIG. 3 because the direction of the flow of the liquid (or blood) is opposite the flow of the extracted liquid (or plasma.).

Another hydrodynamic effect to delay blockage of the separating area is the increase in shear forces acting on the particles and therefore promoting flow by means of an increase in the capillary force by means of which the liquid is transported through the device.

FIG. 5 and FIG. 6 show another version of the microfluidic device where the main channel 1e is extended through a set of parallel microchannels 41 in FIG. 5 or through a set of circular micropillars 51 in FIG. 6. In both, the particles are driven away from the inlet area of the separating area (2) by the induced shear force due to the generated capillary force of the these two micropumps (41 or 51).

FIG. 7 shows a design of a microdevice with three separation stages, including three separate areas 2, 21, 22 to increase the separation efficiency. In FIG. 7, the sample supplied in inlet port 11 flows through a primary main channel 1a which is connected to a main channel 1c having a smaller width through a curved constriction 1b. The sample introduced in the main channel 1 is diverted towards the area 2 and a secondary transport channel 15 which is designed to increase the induced shear force on the particles before reaching the next separating area 21. The three separating areas 2, 21, 22 are connected to a collection channel 3 which is used to collect the extracted liquid (or plasma). The separation occurs while the transport channel it is not completely filled, because once it is filled the rate of flow is so slow that the particles tend to block the inlet in the separating area. In FIG. 7, a final main channel 25 has been added to the end of the transport channel to increase the resistance to the flow and therefore the time it takes to completely fill it. Finally, the final main channel 25 is connected to an outlet port 12 where the concentrated liquid sample is collected.

FIG. 8 shows another three-stage design like the previous design (FIG. 7). In this one, the length of the main channel 1a is reduced to optimize the working time of the device, and the lengths of the transport channels 15 between separating areas are also reduced so that the separating time is faster and the amount of fluid that is extracted can therefore be maximized.

FIG. 9 shows a design with six stages of separation. In this design, the sample supplied in an inlet port 11 flows through a primary main channel 1a which is connected to a channel 1c having a smaller width through a curved constriction 1d. The sample introduced in the channel 1c having a smaller width is diverted towards the separating area 2 and a secondary transport channel 15, and after the separation of these three phases in the first separation part 200, the liquid sample is transmitted to the second separation part 300 by a transport channel 35. Two parallel collection channels 3 are designed for collecting the liquid extracted from each separation part and thus increasing the volume that is separated. In the case of separating plasma from blood, these two distinct channels make it possible to do two different blood analyses simultaneously in the same device.

In accordance with the invention, there is a self-driven microfluidic device for separating particles from a liquid in which the particles are suspended and particularly for blood plasma separation, comprising:

a) at least one transport channel (1) divided in three sections: a first channel section (1a) and a second channel section (1e) having a same width w1 and interconnected by an intermediate channel section (1c) having a width w2, where w2<w1, the first and second channel sections (1a), (1e) being connected to said intermediate section (1c) through a corresponding constriction (1b) (1d) having inner walls curved or not, said transport channel transporting the liquid from an inlet port (11) to an outlet port (12) and avoid clogging in a separating area due to an increased flow in the constriction;

b) at least one separating area (2), which lies completely or partially over the intermediate channel section (1c) having a smaller width, acting as a branch point to divert a desired partial flow of extracted liquid, which is symmetrically located on both sides of the transport channel; and c) at least one collection channel (3) that can include an outlet opening (31) or a reaction chamber, and that is also covered by said separating area (2), wherein the microfluidic device (100) is machined in two parts, a first part (101) containing the separating area acting as filter with a depth (H2) less than the size of particles to be separated and a second part (102) that contains the transport channel (1) and the collection channel (3) and/or a test chamber said channels having a depth (H1) adapted according to a test/analysis to be performed, and wherein both said first part (101) and second part (102) are manufactured using a suitable hydrophilic material or are treated to achieve a hydrophilic behavior in the hydrophobic material.

In addition, the at least one micropump, which includes parallel channels (41) or a collection of micropillars (51), is connected to the end of the second channel section (1e) to promote flow. The transport channel (1) is curved and the separating area (2), which covers either a part of or the whole intermediate channel section (1c) and the separating area (2) is placed either symmetrically or other than symmetrically with regard to said transport channel (1). The at least two electrodes (4) and (5) are placed at the inlet and outlet of the transport channel (1) to apply alternating electrophoretic forces on the particles. The separating area includes an arrangement of the micropillars (2).

The invention claimed is:

1. A self-driven microfluidic device for separating particles from a liquid in which the particles are suspended and particularly for blood plasma separation, comprising:

a) a transport channel (1) divided in three sections: a first channel section (1a) and a second channel section (1e) having a same width w1 and interconnected by an intermediate channel section (1c) having a width w2, where w2<w1, the first and second channel sections (1a), (1e) being connected to said intermediate section (1c) through a corresponding constriction (1b) (1d) having inner walls, said transport channel being configured to transport the liquid from an inlet port (11) to an outlet port (12) and avoid clogging due to an increased flow in the corresponding constriction;

b) a separating area (2), symmetrically located on both sides of the transport channel (1) and lying completely or partially over the intermediate channel section (1c), the separating area (2) being configured to act as a filter; and c) a collection channel (3) including an outlet opening (31) or a reaction chamber, the collection channel (3) being covered by said separating area (2), wherein the microfluidic device (100) is machined in two parts, a first part (101) containing the separating area, the separating area having a depth (H2), and a second part (102) containing the transport channel (1) and the collection channel (3), the transport channel (1) and the collection channel (3) each having a depth (H1) adapted according to a test/analysis to be performed wherein said depth (H2) being smaller than said depth (H1), and wherein both said first part (101) and second part (102) include a hydrophilic material or are treated to achieve a hydrophilic behavior in a hydrophobic material.

2. The microfluidic device for separation of claim 1, further comprising at least one micropump, which includes parallel channels (41) or a collection of micropillars (51), connected to the end of the second channel section (1e) to promote flow.

3. The microfluidic device of claim 1, wherein the transport channel (1) is curved and the separating area (2) covers the whole intermediate channel section (1c).

4. The microfluidic device of claim 2, wherein the transport channel (1) is curved and the separating area (2) covers the whole intermediate channel section (1c).

5. The microfluidic device of claim 1, wherein the transport channel 1 is curved and the separating area (2) covers only a part of the intermediate channel section (1c).

6. The microfluidic device of claim 2, wherein the transport channel 1 is curved and the separating area (2) covers only a part of the intermediate channel section (1c).

7. The microfluidic device of claim 1, wherein at least two electrodes (4) and (5) are placed at the inlet and outlet of the transport channel (1) to apply alternating electrophoretic forces on the particles.

8. The microfluidic device of claim 2, wherein at least two electrodes (4) and (5) are placed at the inlet and outlet of the transport channel (1) to apply alternating electrophoretic forces on the particles.

9. The microfluidic device of claim 1 wherein the separating area includes an arrangement of micropillars (2).

10. The microfluidic device of claim 2 wherein the separating area includes an arrangement of micropillars (2).

* * * * *